US00PP25710P2

(12) United States Plant Patent
Thorup

(10) Patent No.: US PP25,710 P2
(45) Date of Patent: Jul. 14, 2015

(54) ***ALYSSUM* PLANT NAMED 'GOLDEN SPRING'**

(50) Latin Name: *Alyssum wulfenianum*
Varietal Denomination: Golden Spring

(71) Applicant: Ball Horticultural Company, West Chicago, IL (US)

(72) Inventor: Troy Thorup, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 115 days.

(21) Appl. No.: 13/987,956

(22) Filed: Sep. 18, 2013

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Audrey Charles

(57) ABSTRACT

A new and distinct cultivar of *Alyssum* plant named 'Golden Spring', characterized by its bright yellow-colored flowers, greyed-green colored foliage, and moderately vigorous, spreading growth habit, is disclosed.

1 Drawing Sheet

Latin name of genus and species of plant claimed: *Alyssum wulfenianum.*

Variety denomination: 'Golden Spring'.

BACKGROUND OF THE INVENTION

The present invention relates to a new and distinct cultivar of *Alyssum* plant botanically known as *Alyssum wulfenianum* and hereinafter referred to by the cultivar name 'Golden Spring'.

The new cultivar originated in a controlled breeding program in Guadalupe, Calif. during August 2009. The objective of the breeding program was the development of vegetative *Alyssum* cultivars having large bright-colored flowers.

The new *Alyssum* cultivar is the result of open-pollination. The female (seed) parent of the new cultivar is the proprietary *Alyssum wulfenianum* breeding selection coded 2943, unpatented, characterized by its medium yellow-colored flowers, medium green-colored foliage, and moderately vigorous, spreading growth habit. The male (pollen) parent of the new cultivar is unknown. The new cultivar was discovered and selected as a single flowering plant within the progeny of the above stated open-pollination during March 2010 in a controlled environment in Guadalupe, Calif.

Asexual reproduction of the new cultivar by terminal stem cuttings since March 2010 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Golden Spring' as a new and distinct cultivar of *Alyssum* plant:

1. Bright yellow-colored flowers;
2. Greyed-green colored foliage; and
3. Moderately vigorous, spreading growth habit.

Plants of the new cultivar differ from plants of the female parent primarily in having a brighter flower color and larger flower size.

*Alyssum* 'Golden Spring' is the first cultivar of the species and therefore comparison is made to the common species form which is reproduced by seed for the marketplace. In comparison, plants of the new cultivar differ from plants of the species form primarily in flower and inflorescence size. Plants of the new cultivar have larger-sized flowers and larger-sized inflorescences than the common species form.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Golden Spring'. The plants were grown in one-gallon containers for 8 months in a greenhouse in Elburn, Ill. Plants were given two pinches, once at liner stage and once two weeks after transplant.

DETAILED BOTANICAL DESCRIPTION

Figure 1:
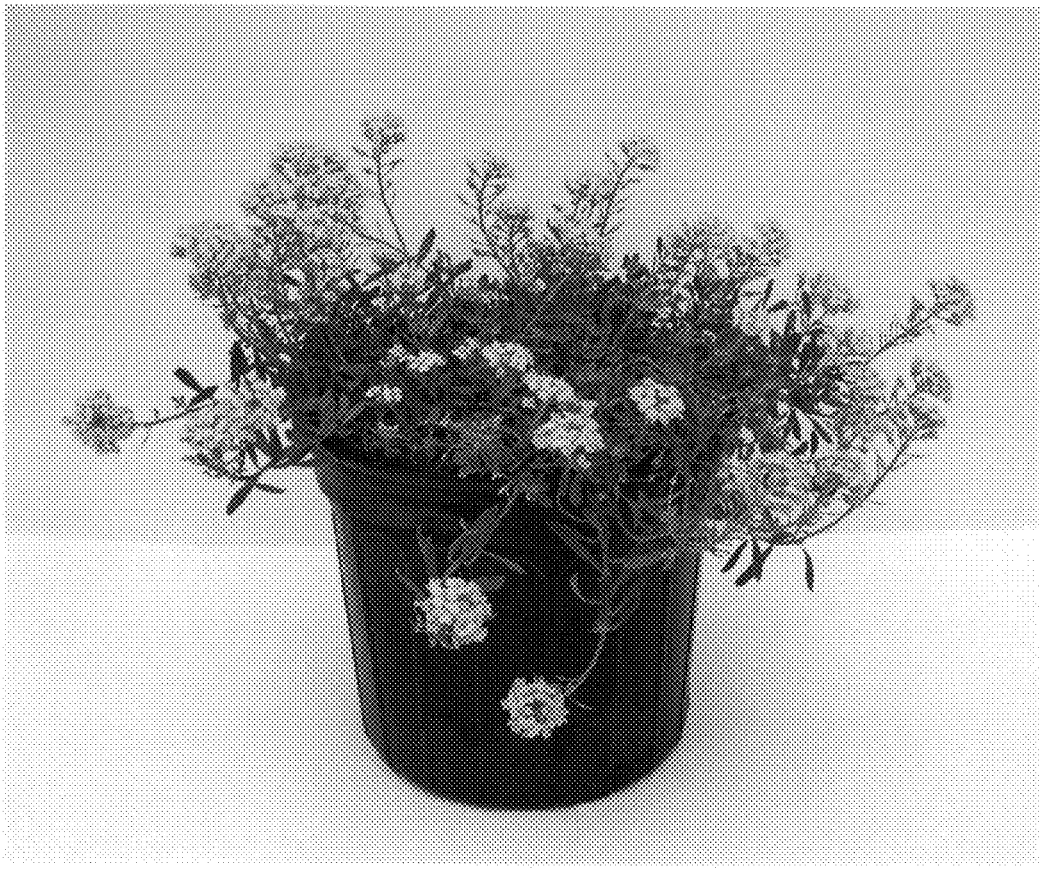
FIG. 1 illustrates a side view of the overall growth and flowering habit of 'Golden Spring'.
Figure 2:
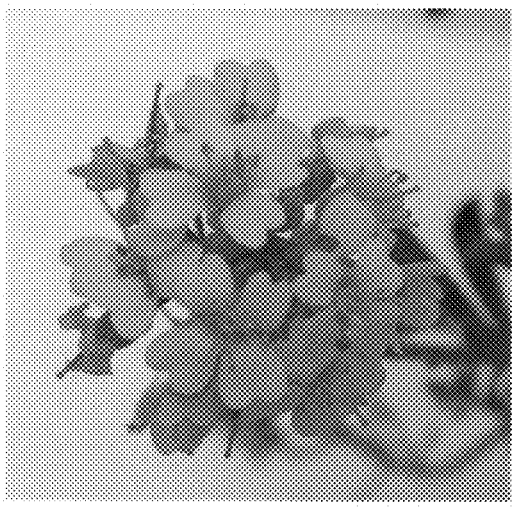
FIG. 2 illustrates a close-up view of an individual inflorescence of 'Golden Spring'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2013 under natural light conditions in West Chicago, Ill. The following descriptions and measurements describe plants produced from cuttings from stock plants and grown in a glass-covered greenhouse under conditions comparable to those used in commercial practice. The plants were grown in Elburn, Ill. in one-gallon containers for 8 months utilizing a soilless growth medium. Plants were given two pinches, once at liner stage and once two weeks after transplant Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Alyssum wulfenianum* cultivar Golden Spring.

Parentage:

*Female parent*.—Proprietary *Alyssum wulfenianum* breeding selection coded 2943, unpatented.

*Male parent*.—Unknown.

Propagation:

*Type cutting*.—Terminal stem.

*Time to initiate roots*.—Approximately 7 to 10 days.

*Time to produce a rooted cutting*.—Approximately 35 to 42 days.

*Root description*.—Fine, fibrous.

*Rooting habit*.—Freely branching.

Plant description:

*Commercial crop time*.—Approximately 26 to 30 weeks from a rooted cutting to finish in a 10 cm pot.

*Growth habit and general appearance*.—Moderately vigorous, spreading.

*Size*.—Height from soil level to top of plant plane: Approximately 12.0 cm. Width: Approximately 33.5 cm.

*Branching habit*.—Somewhat freely branching, pinching enhances lateral branching. Quantity of main branches per plant: Approximately 19.

*Branch*.—Strength: Strong, flexible. Length to base of inflorescence: Approximately 13.0 cm. Diameter: Approximately 2.0 mm. Length of central internode: Approximately 5.0 mm. Texture: Densely pubescent in tufts appressed to stem. Color of young stem: 138B. Color of mature stem: 138B, with a woody overlay of N199B at base.

Foliage description:

*General description*.—Quantity of leaves per main branch: Approximately 13. Fragrance: None. Form: Simple. Arrangement: Alternate.

*Leaves*.—Aspect: At an acute angle to perpendicular to stem. Shape: Narrowly oblanceolate. Margin: Entire. Apex: Acute. Base: Attenuate. Venation pattern: Pinnate. Length of mature leaf: Approximately 2.3 cm. Width of mature leaf: Approximately 5.0 mm. Texture of upper and lower surfaces: Densely pubescent in tufts appressed to leaf. Color of upper surface of young and mature foliage: 137A with midvein of 138A, overall appearance greyed-green due to pubescence. Color of lower surface of young and mature foliage: 138A with midvein of 138B, overall appearance greyed-green due to pubescence.

*Petiole*.—Length: Approximately 4.0 mm. Diameter: Approximately 1.0 mm. Texture: Densely pubescent in tufts appressed to petiole. Color of upper surface: 138A. Color of lower surface: 138B.

Flowering description:

*Flowering habit*.—'Golden Spring' flowers once a year during early spring to late spring under outdoor conditions.

*Lastingness of individual flower on the plant*.—Approximately 3 to 4 days.

Inflorescence description:

*General description*.—Type: Indeterminate raceme. Quantity per plant: Approximately 57. Fragrance: Moderately strong, sweet. Length or height: Approximately 4.5 to 6.5 cm. Width: Approximately 2.7 cm. Quantity of fully open flowers per inflorescence: Approximately 9.

*Peduncle*.—Strength: Strong, flexible. Length: Approximately 2.5 cm. Diameter: Approximately 1.5 cm. Texture: Densely pubescent in tufts appressed to petiole. Color: 138B.

Flower description:

*Type*.—Single, not persistent.

*Bud*.—Rate of opening: Generally takes 2 to 3 days for bud to progress from first color to fully open flower. Quantity per inflorescence: Approximately 3 to 5.

*Bud just before opening*.—Shape: Ovoid. Length: Approximately 3.0 mm. Width: Approximately 2.0 mm. Texture: Densely pubescent in tufts appressed to bud. Color: 144C.

*Corolla*.—Shape: Cruciform. Width: Approximately 8.0 mm. Depth: Approximately 6.0 mm.

*Petals*.—Quantity: 4. Shape: Obovate. Appearance: Dull. Margin: Entire. Apex: Obcordate. Length: Approximately 5.0 mm. Width: Approximately 3.0 mm. Texture of upper and lower surfaces: Glabrous. Color of upper surface when first and fully open: 7A. Color of lower surface when first and fully open: 7B.

*Calyx*.—Shape: Cup-like. Diameter: Approximately 4.0 mm.

*Sepals*.—Quantity per flower: 4. Shape: Ovate. Apex: Acute. Base: Truncate. Length: Approximately 3.0 mm. Width: Approximately 2.0 mm. Texture of upper surface: Glabrous. Texture of lower surface: Densely pubescent in tufts appressed to sepals. Color of upper and lower surfaces: 144D.

*Pedicel*.—Strength: Strong, flexible. Aspect: Acute angle to stem. Length: Approximately 5.0 mm. Diameter: Less than 1.0 mm. Texture: Densely pubescent in tufts appressed to pedicle. Color: 138C.

*Reproductive organs*.—Androecium: Stamen quantity: 6 per flower. Filament length: Approximately 5.0 mm. Filament color: N144D. Anther shape: Bilobed. Anther length: Approximately 1.0 mm. Anther color: 2C. Pollen amount: Moderate. Pollen color: 2D. Gynoecium: Pistil quantity: 1 per flower. Pistil length: Approximately 6.0 mm. Stigma shape: Globular. Stigma length: Less than 1 mm. Stigma color: N144A. Style length: Approximately 4.0 mm. Style color: N144D. Ovary length: Approximately 2.0 mm. Ovary texture: Densely pubescent in tufts appressed to ovary. Ovary color: 144A.

Seed and fruit production: Neither seed nor fruit production has been observed.

Disease and pest resistance: Resistance to pathogens and pests common to *Alyssum* has not been observed.

What is claimed is:

1. A new and distinct cultivar of *Alyssum* plant named 'Golden Spring', substantially as herein illustrated and described.

* * * * *